US012351568B2

(12) United States Patent
Tsuda

(10) Patent No.: US 12,351,568 B2
(45) Date of Patent: *Jul. 8, 2025

(54) METHOD FOR PRODUCING CARBONATE DERIVATIVE

(71) Applicants: NATIONAL UNIVERSITY CORPORATION KOBE UNIVERSITY, Hyogo (JP); MITSUBISHI GAS CHEMICAL COMPANY, INC., Tokyo (JP)

(72) Inventor: Akihiko Tsuda, Hyogo (JP)

(73) Assignees: NATIONAL UNIVERSITY COPORATION KOBE UNIVERSITY, Hyogo (JP); MITSUBISHI GAS CHEMICAL COMPANY, INC., Tokyo (JP)

( * ) Notice: Subject to any disclaimer, the term of this patent is extended or adjusted under 35 U.S.C. 154(b) by 1020 days.

This patent is subject to a terminal disclaimer.

(21) Appl. No.: 17/292,249

(22) PCT Filed: Nov. 14, 2019

(86) PCT No.: PCT/JP2019/044690
§ 371 (c)(1),
(2) Date: May 7, 2021

(87) PCT Pub. No.: WO2020/100977
PCT Pub. Date: May 22, 2020

(65) Prior Publication Data
US 2021/0403409 A1 Dec. 30, 2021

(30) Foreign Application Priority Data
Nov. 15, 2018 (JP) ................. 2018-215003

(51) Int. Cl.
*B01J 19/12* (2006.01)
*C07C 68/00* (2020.01)
*C07C 69/96* (2006.01)
*C07D 317/36* (2006.01)
*C07D 317/38* (2006.01)

(52) U.S. Cl.
CPC .......... *C07D 317/36* (2013.01); *B01J 19/123* (2013.01); *C07D 317/38* (2013.01)

(58) Field of Classification Search
CPC .................................................... B01J 19/123
See application file for complete search history.

(56) References Cited

U.S. PATENT DOCUMENTS

| | | | |
|---|---|---|---|
| 4,346,210 A | 8/1982 | Alewelt et al. | |
| 4,405,423 A | 9/1983 | Freund | |
| 5,728,773 A | 3/1998 | Jing et al. | |
| 5,929,169 A | 7/1999 | Jing et al. | |
| 7,138,479 B2 | 11/2006 | Dhara et al. | |
| 11,130,728 B2 * | 9/2021 | Tsuda | C07D 317/38 |
| 11,167,259 B2 * | 11/2021 | Tsuda | C08G 71/04 |
| 2006/0135662 A1 | 6/2006 | Mullen | |
| 2007/0197826 A1 | 8/2007 | Braun et al. | |
| 2011/0245527 A1 | 10/2011 | Ooms et al. | |
| 2015/0285954 A1 | 10/2015 | Ishizuka et al. | |
| 2016/0032046 A1 | 2/2016 | Shirota et al. | |
| 2020/0079723 A1 | 3/2020 | Tsuda | |
| 2020/0122114 A1 | 4/2020 | Tsuda | |
| 2022/0002234 A1 | 1/2022 | Tsuda et al. | |

FOREIGN PATENT DOCUMENTS

| | | |
|---|---|---|
| JP | 6-179743 | 6/1994 |
| JP | 7-10811 | 1/1995 |
| JP | 8-89975 | 4/1996 |
| JP | 10-77339 | 3/1998 |
| JP | 10-291965 | 11/1998 |
| JP | 11-152328 | 6/1999 |
| JP | 2000-319230 | 11/2000 |
| JP | 2001-129397 | 5/2001 |
| JP | 2001-512515 | 8/2001 |
| JP | 2003-220332 | 8/2003 |
| JP | 2007-527841 | 10/2007 |
| JP | 2013-181028 | 9/2013 |
| JP | 2020-83882 | 6/2020 |
| JP | 7041925 | 3/2022 |
| SU | 1020006 | 5/1983 |
| WO | 2012/073970 | 6/2012 |
| WO | 2014/171367 | 10/2014 |
| WO | 2015/156245 | 10/2015 |
| WO | WO-2015156245 A1 * | 10/2015 ............. C07C 67/39 |

(Continued)

OTHER PUBLICATIONS

Office Action issued Dec. 18, 2023 in U.S. Appl. No. 17/292,194.
Saudi Arabian Office Action issued Dec. 25, 2023 in Saudi Arabian Patent Application No. 521421871, with English translation.
International Search Report issued Jul. 17, 2018 in International (PCT) Application No. PCT/JP2018/017348.
Kuwahara et al., "Photo-recycling reactions of Halomethanes (1): Synthesis of Urea Derivatives from Chloroform and Primary Amines", Abstracts of the meeting of The Chemical Society of Japan, 92nd, 2012, p. 1251, 2 K2-14, with partial English translation.
Kuwahara et al., "Photo-recycling reactions of Halomethanes (2): Synthesis of Carbonate Derivatives from Chloroform and Phenol Derivatives", Abstracts of the meeting of The Chemical Society of Japan, 92nd, 2012, p. 1251, 2 K2-16, with partial English translation.
Extended European Search Report issued Nov. 12, 2020 in European Patent Application No. 18802405.3.
Singapore Search Report and Written Opinion issued Feb. 11, 2021 in Singaporean Patent Application No. 11201909670Y.

(Continued)

*Primary Examiner* — Matthew P Coughlin
(74) *Attorney, Agent, or Firm* — Wenderoth, Lind & Ponack, L.L.P.

(57) ABSTRACT

The objective of the present invention is to provide a method for producing a polycarbonate safely and efficiently even without using a base. The method for producing a carbonate derivative according to the present invention is characterized in comprising the step of irradiating a high energy light to a composition comprising the halogenated methane and the hydroxy group-containing compound in the presence of oxygen, wherein a molar ratio of a total usage amount of the hydroxy group-containing compound to 1 mole of the halogenated methane is 0.05 or more.

5 Claims, 1 Drawing Sheet

(56) References Cited

FOREIGN PATENT DOCUMENTS

| WO | 2018/211952 | 11/2018 |
|---|---|---|
| WO | 2018/211953 | 11/2018 |
| WO | 2020/050368 | 3/2020 |
| WO | 2020/100970 | 5/2020 |
| WO | 2020/100971 | 5/2020 |

OTHER PUBLICATIONS

Search Report and Office Action issued Jun. 15, 2021 in Russian Patent Application No. 2019138715, with English translation.
Office Action issued Feb. 10, 2022 in corresponding Russian Application No. 2021116822, with English-language translation.
Office Action issued Feb. 11, 2022 in Russian Application No. 2021116821, with English-language translation.
Office Action issued May 31, 2024 in U.S. Appl. No. 17/292,194.
Office Action issued Jul. 17, 2022 in Singapore Application No. 11202104285Q.
Office Action issued Aug. 4, 2022 in Chinese Application No. 201980074609.4, with English translation.
Written Opinion issued Sep. 6, 2022 in corresponding Singapore Application No. 11202104284V.
Taiwanese Office Action dated Nov. 25, 2022 in corresponding Taiwanese Patent Application No. 108141360, with English translation.
Office Action dated Sep. 6, 2023 in related Singapore Patent Application No. 11202104285Q.
Notice of Reasons for Refusal issued Sep. 26, 2023 in corresponding Japanese Patent Application No. 2020-556165, with English language translation.
Office Action issued Oct. 9, 2023 in corresponding Singapore Patent Application No. 11202104284V.
Extended European Search Report issued Nov. 30, 2021 in corresponding European Patent Application No. 19883691.8.
Extended European Search Report issued Dec. 9, 2021 in corresponding European Patent Application No. 19883406.1.
Kuwahara et al., "Photochemical Molecular Storage of $Cl_2$, HCl, and $COCl_2$: Synthesis of Organochlorine Compounds, Salts, Ureas, and Polycarbonate with Photodecomposed Chloroform", Organic Letters, 2012, vol. 14, No. 13, pp. 3376-3379.
Communication pursuant to Article 94(3) EPC issued Jul. 21, 2023 in European Patent Application No. 19883406.1.
Office Action issued Jun. 7, 2023 in corresponding Saudi Arabian Patent Application No. 521421868, with English language translation.
Office Action issued Dec. 16, 2022 in Taiwanese Application No. 108141365, with English-language translation.
Office Action issued Jan. 9, 2023 in Chinese Patent Application No. 201980074609.4, with English-language translation.
International Search Report issued Jan. 21, 2020 in International (PCT) Application No. PCT/JP2019/044686.
International Search Report issued Jan. 28, 2020 in International (PCT) Application No. PCT/JP2019/044690.
Ohkuma et al., "Detection of aromatic primary amines by a photochemical reaction with pyridine", The Journal of the Japan Society for Analytical Chemistry, 1975, vol. 24, pp. 385-387.
Tsurugi et al., Journal of the Society of Rubber Science and Technology, Japan, 1970, vol. 43, No. 5, pp. 337-346, with partial English translation.
Herbich et al., "Mechanisms of fluorescence quenching by hydrogen bonding in various aza aromatics", J. Photochem. Photobiol. A: Chem., 1994, vol. 80, pp. 157-160.
Hoggard et al., "Catalysis of the photodecomposition of carbon tetrachloride in ethanol by an Amberlite anion exchange resin", Journal of Catalysis, 2010, vol. 275, pp. 243-249.
Brooke et al., "A Photocatalyzed Synthesis of Dialkyl Carbonates from Phosgene Generated in situ", Current Catalysis, 2015, vol. 4, No. 1, pp. 12-19.
Office Action issued Mar. 7, 2023 in Chinese Patent Application No. 201980074645.0, with English-language translation.
Office Action issued Mar. 20, 2023 in Taiwanese Patent Application No. 108141365, with English-language translation.
Office Action issued May 9, 2023 in Japanese Patent Application No. 2020-556163, with English-language translation.
Office Action issued Sep. 12, 2024 in Korean Patent Application No. 10-2021-7016988, with English-language translation.
International Search Report issued Apr. 5, 2022 in International (PCT) Application No. PCT/JP2022/002661, with English- language Translation.
Office action issued Nov. 29, 2022 in Japanese Application No. 2022-542485, with English language translation.
Office action issued Sep. 13, 2022 in Japanese Application No. 2022-542485, with English language translation.
Office Action issued Sep. 26, 2024 in Korean Patent Application No. 10-2021-701697, with English-language Translation.
Office Action issued Jul. 7, 2021 in European Patent Application No. 18 801 749.5.
Extended European Search Report issued Nov. 19, 2020 in European Patent Application No. 18801749.5.
International Search Report issued Jul. 10, 2018 in International (PCT) Application No. PCT/JP2018/017349.
International Search Report issued Nov. 10, 2020 in International Application No. PCT/JP2022/033284.
Office Action issued May 25, 2021 in U.S. Appl. No. 16/605,635.
Extended European Search Report issued Dec. 8, 2023 in European Patent Application No. 20859957.1.
Office Action issued Apr. 20, 2023 in Chinese Patent Application No. 202080061004.4, with English-language Translation.
Office Action issued Jun. 3, 2024 in Taiwanese Patent Application No. 109130332, with English language translation.
C.W. Montgomery, et al., "The Photochemical Decomposition of Phosgene", Contribution From The Chemical Laboratory Of The University Of California, J. Am. Chem. Soc., 1934, vol. 56, pp. 1089-1092.
Yuki Kuwahara, et al., "Photochemical Molecular Storage of $Cl_2$, HCl, and $COCl_2$: Synthesis of Organochlorine Compounds, Salts, Ureas, and Polycarbonate with Photodecomposed Chloroform", Organic Letters, 2012, vol. 14, No. 13, pp. 3376-3379.
Schoorl; van der Berg, "RX-ID 6330183," Chemisches Zentralblatt, 1905, vol. 76, No. II, p. 1623.
Alippi, A. et al., "Ultrasound cavitation in sonochemistry: decomposition of carbon tetrachloride in aqueous solutions of potassium iodide", Ultrasonics, vol. 30, No. 3, 1992, pp. 148-151.
Cheung, Michael H. et al., "Sonochemical Destruction of Chlorinated Hydrocarbons in Dilute Aqueous Solution", Environmental Science & Technology. vol. 25, No. 8, 1991, pp. 1510-1512.
Office Action issued Jan. 9, 2025, in Russian Patent Application No. 2023123329, with English translation.
Office Action issued Feb. 14, 2025 in Korean Patent Application No. 10-2022-7007456, with English-language Translation.
Office Action issued Mar. 3, 2025 in U.S. Appl. No. 17/639,751.
Office Action issued May 16, 2025 in Korean Patent Application No. 10-2023-7025702, with English-language translation.

* cited by examiner

[FIG. 1]
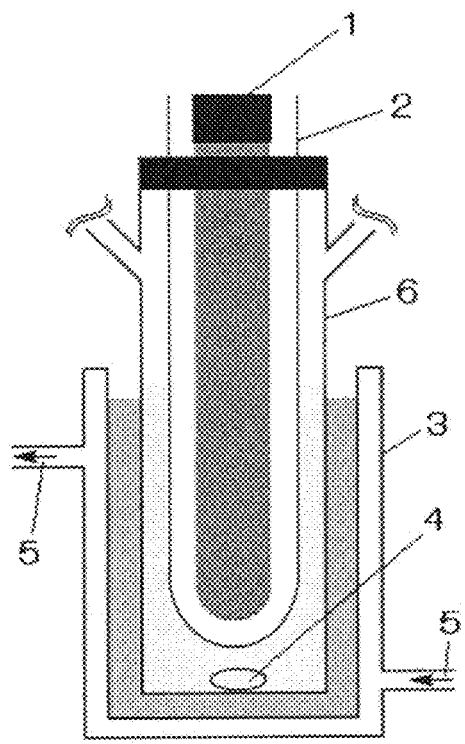
[FIG. 2]
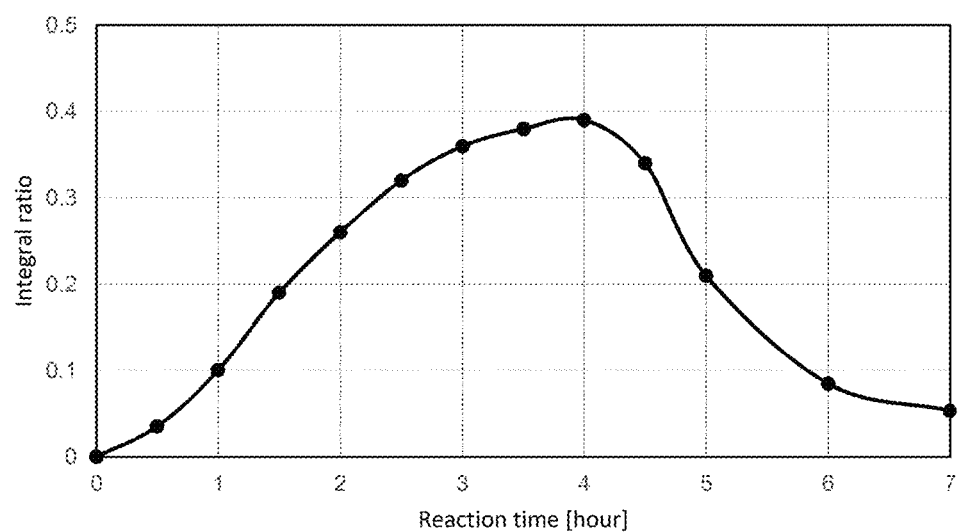

METHOD FOR PRODUCING CARBONATE DERIVATIVE

TECHNICAL FIELD

The present invention relates to a method for producing a carbonate derivative safely and efficiently.

BACKGROUND ART

A linear carbonate among a carbonate derivative has been conventionally used as a solvent or the like. A production amount of a linear carbonate is particularly increased in recent years, since a linear carbonate is used as a non-aqueous solvent for an electrolyte of a lithium ion secondary battery. In addition, a polycarbonate, which is a condensate of carbonic acid and a bisphenol compound, is widely used as an engineering plastic excellent in transparency and impact resistance.

A carbonate derivative is generally produced from phosgene and a hydroxy group-containing compound. Phosgene is however very toxic. For example, phosgene is easily reacted with water to generate hydrogen chloride and has a history of being used as poisonous gas. Alternatively, a carbonate derivative is produced by reacting carbon monoxide, an alcohol and oxygen, but this method has a problem that an expensive catalyst or toxic carbon monoxide at high pressure must be used. A method for safely producing a carbonate ester and a polycarbonate is therefore variously studied.

For example, Patent document 1 discloses a method for producing a target carbonate derivative by subjecting a carbonate ester to a transesterification reaction in the presence of a catalyst. This method however is not an essential solution, since the method has a problem of how to produce the carbonate ester as a raw material compound. In addition, the method has a problem that an expensive catalyst must be used and a problem of a reverse reaction and a side reaction due to a remaining catalyst.

Patent document 2 discloses a method for producing a carbonate derivative from an epoxy compound and carbon dioxide in the presence of a catalyst. Phosgene and carbon monoxide are not needed to be used in this method but an expensive catalyst must be used and a high pressure carbon dioxide is needed. In addition, the polycarbonate producible by this method is limited, and there is also a problem of a side product.

The inventor of the present invention has developed a method for producing a halogenated formate ester by subjecting a halogenated hydrocarbon and an alcohol to an oxidative photoreaction (Patent document 3) and a method for producing a halogenated formate ester by irradiating a light to chloroform in the presence of oxygen to obtain a mixture containing phosgene and reacting an alcohol with the mixture without isolating phosgene (Patent document 4).

PRIOR ART DOCUMENT

Patent Document

Patent document 1: JP H7-10811 A
Patent document 2: JP 2001-129397 A
Patent document 3: WO 2015/156245
Patent document 4: JP 2013-181028 A

DISCLOSURE OF THE INVENTION

Problems to be Solved by the Invention

Phosgene is generally used for producing a carbonate derivative as described above. Even if phosgene is not used in a certain production method, such a production method has problems that the other toxic compound and an expensive catalyst are used or phosgene must be used for producing a raw material compound.

The reason why a halogenated formate ester can be obtained by the invention of Patent document 3 is considered to be that the reaction does not further proceed without using a base. On the one hand, for example, when a base is used in the case of a polycarbonate, a remaining base may cause coloration and decomposition, and the value as an optical material may be decreased in some cases. In addition, hydrogen chloride generated from a halogenated hydrocarbon is preferably recovered to be reused. Specifically, recovered hydrogen chloride is decomposed into chlorine and water, and the obtained chlorine is reacted with methane to produce a chloro methane such as chloroform to be reused. But an electrolytic treatment is needed to recover hydrogen chloride, since when a base is used, a salt is generated from hydrogen chloride.

Accordingly, the objective of the present invention is to provide a method for producing a polycarbonate safely and efficiently even without using a base.

Means for Solving the Problems

The inventor of the present invention repeated intensive studies in order to solve the above-described problems. As a result, the inventor completed the present invention by finding that a carbonate derivative can be amazingly produced without using a base in a safe and efficient manner by subjecting a halogenated methane and the specific amount of a hydroxy group-containing compound to a photoreaction in the presence of oxygen. A halogenated hydrocarbon has been conventionally considered not to be decomposed by increasing a ratio of a hydroxy group-containing compound to the halogenated hydrocarbon, since a hydroxy group-containing compound is known as a stabilizer to prevent a halogenated hydrocarbon from being decomposed. On the one hand, it was very surprising that even when a base is not used, a reaction proceeds from a halogenated formate ester and a carbonate derivative is efficiently generated.

The present invention is hereinafter described.

[1] A method for producing a carbonate derivative, the method comprising the step of irradiating a high energy light to a composition comprising a halogenated methane and a hydroxy group-containing compound in the presence of oxygen, wherein a molar ratio of a total usage amount of the hydroxy group-containing compound to 1 mole of the halogenated methane is 0.05 or more, wherein the hydroxy group-containing compound is represented by the following formula (i) and the carbonate derivative is a linear carbonate derivative represented by the following formula (I), or the hydroxy group-containing compound is represented by the following formula (ii) and the carbonate derivative is a carbonate derivative comprising a unit represented by the following formula (II-1) or a cyclic carbonate derivative represented by the following formula (II-2):

 (i)

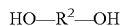 (ii)

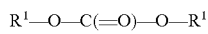 (I)

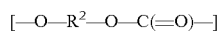 (II-1)

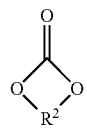 (II-2)

wherein
$R^1$ is a monovalent $C_{1-200}$ organic group optionally comprising a hetero atom,
$R^2$ is a divalent $C_{1-200}$ organic group optionally comprising a hetero atom.
[2] The method according to the above [1], wherein the halogenated methane is chloroform.
[3] The method according to the above [1] or [2], further comprising the step of stirring the composition without irradiating the high energy light.
[4] The method according to any one of the above [1] to [3], wherein the high energy light comprises a light having a wavelength of 180 nm or more and 280 nm or less.
The method according to any one of the above [1] to [4], wherein two or more kinds of the hydroxy group-containing compound are used.

Effect of the Invention

It is not needed in the present invention method that an expensive catalyst and a highly toxic compound such as phosgene and carbon monoxide are used as a raw material compound. In addition, a high quality carbonate derivative can be obtained, since a base is not needed to be used and does not remain in the carbonate derivative as a target compound. The present invention method is, therefore, industrially very useful as a technology to safely and efficiently produce a useful high quality polycarbonate.

BRIEF DESCRIPTION OF THE DRAWINGS

FIG. 1 is a schematic diagram to demonstrate one example of the constitution of a reaction apparatus usable in the present invention method.

FIG. 2 is a graph to demonstrate a time-dependent change of a ratio of a cyclic carbonate/ethylene glycol in the reaction mixture in the case where ethylene glycol was used as a hydroxy group-containing compound.

MODE FOR CARRYING OUT THE INVENTION

A high energy light is irradiated to a composition comprising a halogenated methane and a hydroxy group-containing compound in the presence of oxygen in the method for producing a carbonate derivative according to the present invention.

1. Halogenated Methane

The halogenated methane may be decomposed due to the high energy light and oxygen into a halogenated carbonyl or a halogenated carbonyl-like compound and reacted with the hydroxy group-containing compound to generate a carbonate derivative in the reaction of the present invention. Even if a toxic halogenated carbonyl compound is generated, the halogenated carbonyl compound is immediately reacted with the hydroxy group-containing compound due to extremely high reactivity. As a result, the halogenated carbonyl compound is not leaked outside the reaction mixture, or even if the halogenated carbonyl is leaked, the leakage amount may be small. In particular, since a ratio of a usage amount of the hydroxy group-containing compound to the halogenated methane is relatively high in the present invention, the generated halogenated carbonyl compound may be immediately reacted with the hydroxy group-containing compound. For example, phosgene as a halogenated carbonyl is very toxic and strict regulations are imposed on the transportation thereof; on the one hand, the halogenated methane is certainly not so dangerous.

A halogenated methane which is liquid under an atmospheric temperature and an atmospheric pressure is used as an organic solvent or the like in a large amount, but causes environmental pollution such as air pollution and ozone layer destruction when released to the atmosphere. The present invention is a technology to produce a useful compound by a photolysis of a halogenated methane and greatly contributes to both an industry and an environmental science.

The halogenated methane is methane substituted by one or more halogeno groups selected from the group consisting of fluoro, chloro, bromo and iodo. As described above, the halogenated methane may be decomposed by a high energy light and oxygen, and may act similarly to a halogenated carbonyl in the present invention.

An example of the halogenated methane includes a fluoro methane such as trifluoro methane; a chloro methane such as dichloromethane, chloroform and carbon tetrachloride; a bromo methane such as dibromomethane and bromoform; an iodo methane such as iodomethane and diiodomethane; and chlorodifluoromethane, dichlorofluoromethane, trichlorofluoromethane and bromofluoromethane.

The halogenated methane may be appropriately selected depending on the target reaction and the desired product. One halogenated methane may be used by itself, or two or more of the halogenated methanes may be used in combination. It is preferred that only one kind of the halogenated methane is used depending on the target compound. The halogenated methane having a chloro is preferred.

The halogenated methane usable in the present invention method may be a recovered halogenated methane which has been once used as, for example, a solvent. It is preferred that such a used halogenated methane is purified to some extent for use, since if a large amount of an impurity and water is contained, the reaction may be possibly inhibited. For example, it is preferred that a water-soluble impurity is removed by washing with water and then the halogenated methane is dried by anhydrous sodium sulfate, anhydrous magnesium sulfate or the like. An excessive purification by which the productivity becomes less is not needed, since even when water is contained, the reaction may proceed. The water content is preferably 0 mass % or more, more preferably 0.0001 mass % or more, and preferably 0.5 mass % or less, more preferably 0.2 mass % or less, and even more preferably 0.1 mass % or less. The halogenated methane to be reused may contain a degradant of the halogenated methane.

2. Hydroxy Group-Containing Compound

The "hydroxy group-containing compound" in this disclosure means a compound which has a nucleophilic hydroxy group and which is represented by the formula (i) or the formula (ii). The compounds are respectively abbreviated as "the hydroxy group-containing compound (i)" and "the hydroxy group-containing compound (ii)" in some cases. The hydroxy group-containing compound used in the present invention does not have a fluoro as a substituent, and as a result, the carbonate derivative produced by the present invention method also does not have a fluoro as a substituent. In addition, even if a base is not used, the reaction to obtain the carbonate derivative can proceed by using the specific amount of the hydroxy group-containing compound.

In the present invention, when the hydroxy group-containing compound (i) is used, the obtained carbonate derivative is a linear carbonate derivative represented by the formula (I) (hereinafter, abbreviated as "the linear carbonate (I)" in some cases), and when the hydroxy group-containing compound (ii) is used, the obtained carbonate derivative is a carbonate derivative comprising a unit represented by the formula (II-1) (hereinafter, abbreviated as "the polycarbonate derivative (II-2)" in some cases) or a cyclic carbonate derivative represented by the formula (II-2) (hereinafter, abbreviated as "the cyclic carbonate derivative (II-2)" in some cases).

The hydroxy group-containing compound (i) and the hydroxy group-containing compound (ii) used as the raw material compound in the production method of the present invention and the linear carbonate (I), the polycarbonate derivative (11-1) and the cyclic carbonate derivative (II-2) as the target compound are described as follows:

  (i)

  (ii)

  (I)

  (II-1)

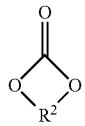  (II-2)

wherein
$R^1$ is a monovalent $C_{1-200}$ organic group optionally comprising a hetero atom,
$R^2$ is a divalent $C_{1-200}$ organic group optionally comprising a hetero atom.

For example, the monovalent organic group having a carbon number of 1 or more and 200 or less is described as a "monovalent $C_{1-200}$ organic group" in this disclosure. The other group and the other compound are similarly described.

An example of the monovalent $C_{1-200}$ organic group optionally comprising a hetero atom includes a monovalent $C_{1-20}$ aliphatic hydrocarbon group optionally having a substituent α, a $C_{3-20}$ cycloalkyl group optionally having a substituent α, a monovalent $C_{6-32}$ aromatic hydrocarbon group optionally having a substituent β, a 5-20 membered saturated heterocyclic group optionally having a substituent β, a 5-20 membered aromatic heterocyclic group optionally having a substituent β and a (poly)alkylene glycol monoalkyl ether group.

The "monovalent $C_{1-20}$ aliphatic hydrocarbon group" is a linear or branched monovalent aliphatic hydrocarbon group having a carbon number of 1 or more and 20 or less, and exemplified by a $C_{1-20}$ alkyl group, a $C_{1-20}$ alkenyl group and a $C_{2-20}$ alkynyl group. An example of the $C_{1-20}$ alkyl group includes methyl, ethyl, n-propyl, isopropyl, n-butyl, isobutyl, s-butyl, t-butyl, n-pentyl, n-hexyl, n-octyl, n-decyl, n-pentadecyl and n-icosyl. The $C_{1-20}$ aliphatic hydrocarbon group is preferably a $C_{1-10}$ alkyl group or a $C_{1-6}$ alkyl group, more preferably a $C_{1-4}$ alkyl group or a $C_{1-2}$ alkyl group, and even more preferably methyl. An example of the $C_{2-20}$ alkenyl group includes ethenyl (vinyl), 1-propenyl, 2-propenyl (allyl), isopropenyl, 2-butenyl, 3-butenyl, isobutenyl, pentenyl, hexenyl, octenyl, decenyl, pentadecenyl and icosenyl. The $C_{2-20}$ alkenyl group is preferably a $C_{2-10}$ alkenyl group or a $C_{2-6}$ alkenyl group, and more preferably ethenyl (vinyl) or 2-propenyl (allyl). An example of the $C_{2-20}$ alkynyl group includes ethynyl, 1-propynyl, 2-propynyl, 2-butynyl, 3-butynyl, pentynyl, hexynyl, octynyl, decynyl, pentadecynyl and icosynyl. The $C_{2-20}$ alkynyl group is preferably a $C_{2-10}$ alkynyl group or a $C_{2-6}$ alkynyl group, and more preferably $C_{2-4}$ alkynyl group or a $C_{2-3}$ alkynyl group.

The "$C_{3-20}$ cycloalkyl group" is a monovalent cyclic saturated aliphatic hydrocarbon group having a carbon number of 3 or more and 20 or less and exemplified by cycropropyl, cyclobutyl, cyclopentyl, cyclohexyl and adamantyl. The group is preferably a $C_{3-10}$ cycloalkyl group.

The "monovalent $C_{6-32}$ aromatic hydrocarbon group" is a monovalent aromatic hydrocarbon group having a carbon number of 6 or more and 32 or less, and exemplified by phenyl; a condensed polycyclic aromatic hydrocarbon group such as indenyl, naphthyl, biphenyl, acenaphthenyl, fluorenyl, phenalenyl, phenanthrenyl, anthracenyl, triphenylenyl, pyrenyl, chrysenyl, naphthacenyl, perylenyl, biphenyl, pentaphenyl, pentacenyl, tetraphenylenyl, hexaphenyl, hexacenyl, rubicenyl, coronenyl, trinaphthylenyl, heptaphenyl, heptaceryl, pyranthrenyl and ovalenyl; and terphenylene and quarter phenylene, and is preferably a monovalent $C_{6-12}$ aromatic hydrocarbon group and more preferably phenyl.

The "5-20 membered saturated heterocyclic group" means a saturated cyclic group which contains one or more hetero atoms such as an oxygen atom, a sulfur atom and a nitrogen atom and in which the total number of the carbon atom and hetero atom forming the ring is 5 or more and 20 or less. The group may be a monocyclic group having only one ring, or a directly connected polycyclic group, a condensed cyclic group, a bridged cyclic group or a spirocyclic group formed by connecting two or more groups each other with a single bond. An example of the 5-20 membered saturated heterocyclic group includes oxiranyl, aziridinyl, tetrahydrofuranyl, tetrahydrothiophenyl, pyrrolidinyl, oxathiolanyl, piperidinyl and isosorbide.

The "5-20 membered aromatic heterocyclic group" means a 5 membered aromatic heterocyclic group, a 6 membered aromatic heterocyclic group, a condensed aromatic heterocyclic group and the like which contain one or more hetero atoms such as a nitrogen atom, an oxygen atom and a sulfur atom, and is exemplified by a 5 membered aromatic heterocyclic group such as pyrrolyl, imidazolyl, pyrazolyl, thienyl, furyl, oxazolyl, isoxazolyl, thiazolyl, isothiazolyl and thiadiazolyl; a 6 membered aromatic heterocyclic group such as pyridinyl, pyrazinyl, pyrimidinyl and pyridazinyl; and a condensed aromatic heterocyclic group such as indolyl, isoindolyl, quinolinyl, isoquinolinyl, benzofuranyl, isobenzofuranyl and chromenyl.

The "(poly)alkylene glycol monoalkyl ether group" means an alkylene glycol monoalkyl ether group or a polyalkylene glycol monoalkyl ether group, and is represented by the following formula. The carbon number of the (poly)alkylene glycol monoalkyl ether group is mainly adjusted to 200 or less by the carbon number of $R^4$ and m. For example, when the carbon number of $R^4$ is 8, m is an integer of 24 or less.

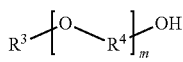

wherein
$R^3$ is a $C_{1-8}$ alkyl group,
$R^4$ is a $C_{1-3}$ alkylene group,
m is an integer of 1 or more and 50 or less.

The $C_{1-3}$ alkyl group is a linear or branched monovalent saturated aliphatic hydrocarbon group having a carbon number of 1 or more and 8 or less, and is preferably a $C_{1-6}$ alkyl group or a $C_{1-4}$ alkyl group, more preferably a $C_{1-2}$ alkyl group and even more preferably methyl.

The $C_{1-8}$ alkylene group is a linear or branched divalent saturated aliphatic hydrocarbon group having a carbon number of 1 or more and 8 or less, and is exemplified by methylene, ethylene, methylmethylene, n-propylene, methylethylene, n-butylene, methylpropylene, dimethylethylene, n-pentylene and n-hexylene, and is preferably a $C_{1-6}$ alkylene group or a $C_{1-4}$ alkylene group and more preferably a $C_{2-4}$ alkylene group.

An example of the substituent α includes one or more substituents selected from a $C_{1-6}$ alkoxy group, a $C_{1-7}$ acyl group, a halogeno group, a nitro group, a cyano group and a carbamoyl group, and an example of the substituent β includes one or more substituents selected from a $C_{1-6}$ alkyl group, a $C_{1-6}$ alkoxy group, a $C_{1-7}$ acyl group, a halogeno group, a nitro group, a cyano group and a carbamoyl group.

The "$C_{1-6}$ alkoxy group" is a linear or branched monovalent aliphatic hydrocarbon oxy group having a carbon number of 1 or more and 6 or less. The $C_{1-6}$ alkoxy group is exemplified by methoxy, ethoxy, n-propoxy, isopropoxy, n-butoxy, isobutoxy, t-butoxy, n-pentoxy and n-hexoxy, preferably a $C_{1-4}$ alkoxy group, more preferably a $C_{1-2}$ alkoxy group, and even more preferably methoxy.

The "$C_{1-7}$ acyl group" is a remaining atomic group which is obtained by removing OH from an aliphatic carboxylic acid having a carbon number of 1 or more and 7 or less, and is exemplified by formyl, acetyl, ethylcarbonyl, n-propylcarbonyl, isopropylcarbonyl, n-butylcarbonyl, isobutylcarbonyl, t-butylcarbonyl, n-pentylcarbonyl and n-hexylcarbonyl, and is preferably a $C_{1-4}$ acyl group and more preferably acetyl.

The halogeno group is one or more groups selected from the group consisting of chloro, bromo and iodo, and is preferably chloro or bromo and more preferably chloro.

The substituent number of the substituent α is not particularly restricted as long as the substitution is possible and is exemplified by 1 or more and 20 or less. The substituent number is preferably 10 or less, more preferably 5 or less or 3 or less and even more preferably 2 or less or 1.

The substituent number of the substituent 3 is not particularly restricted as long as the substitution is possible and is exemplified by 1 or more and 10 or less. The substituent number is preferably 5 or less, more preferably 3 or less and even more preferably 2 or less or 1.

An example of the hydroxy group-containing compound (i) includes phenol and a derivative thereof, such as phenol, 2-chlorophenol, 3-chlorophenol, 4-chlorophenol, 2-bromophenol, 3-bromophenol, 4-bromophenol, 2-methylphenol, 3-methylphenol and 4-methylphenol; a $C_{3-10}$ cycloalkanol such as cyclohexanol; benzyl alcohol and a derivative thereof, such as benzyl alcohol and 2,6-benzyl alcohol; an alkylene glycol mono($C_{1-4}$ alkyl) ether such as ethylene glycol monomethyl ether and propylene glycol monomethyl ether; and an oligo alkylene glycol mono($C_{1-4}$ alkyl) ether such as diethylene glycol monomethyl ether, triethylene glycol monomethyl ether and tetraethylene glycol monomethyl ether.

One kind of the hydroxy group-containing compound (i) may be used by itself, or two or more kinds of the hydroxy group-containing compound (i) may be used in combination. For example, when two or more kinds of the hydroxy group-containing compound (i) are used in combination, an asymmetric linear carbonate derivative can be synthesized. It is however preferred to use only one kind of the hydroxy group-containing compound (i) by itself in terms of a production efficiency or the like.

An example of the hydroxy group-containing compound (ii) includes the following hydroxy group-containing compound (ii-1):

HO—$R^5$—OH     (ii-1)

wherein $R^5$ is a divalent $C_{1-20}$ aliphatic hydrocarbon group optionally having substituent α, a $C_{3-20}$ cycloalkylene group optionally having substituent α, a divalent $C_{6-32}$ aromatic hydrocarbon group optionally having substituent β, a 5-20 membered saturated heterocyclylene group optionally having substituent (3, a 5-20 membered aromatic cyclocyclylene group optionally having substituent β or a divalent (poly)alkylene glycol group.

The above-described divalent $C_{1-20}$ aliphatic hydrocarbon group, $C_{3-20}$ cycloalkylene group, divalent $C_{6-32}$ aromatic hydrocarbon group, 5-20 membered saturated cyclocyclylene group, 5-20 membered aromatic heterocyclylene group and divalent (poly)alkylene glycol group are respectively exemplified by a divalent organic group corresponding to a monovalent monovalent $C_{1-20}$ aliphatic hydrocarbon group, a $C_{3-21}$ cycloalkyl group, a monovalent $C_{6-32}$ aromatic hydrocarbon group, a 5-20 membered saturated heterocyclic group, a 5-20 membered aromatic heterocyclic group and a (poly)alkylene glycol monoalkyl ether group. For example, an example of the 5-20 membered heterocyclylene group includes the following groups.

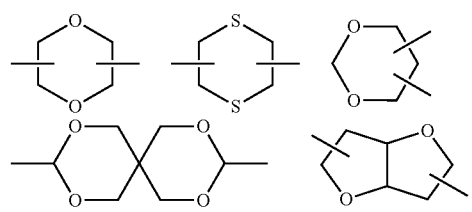

An example of the divalent (poly)alkylene glycol group includes the group represented by the following formula:

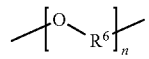

wherein $R^6$ is a $C_{1-8}$ alkylene group, and n is an integer of 1 or more and 50 or less.

An example of the hydroxy group-containing compound (ii) includes a glycol compound such as 1,2-ethane diol, 1,2-propane diol, 1,3-propane diol and 1,4-butane diol; a hydroxy benzene compound such as catechol and resorcinol; and a dihydroxy heteroaryl compound such as 4,6-dihydroxy-2-methylpyrimidine and 3,6-dihydroxy-4-methylpyridazine.

In addition, an example of the hydroxy group-containing compound (ii) includes the following hydroxy group-containing compound (ii-2):

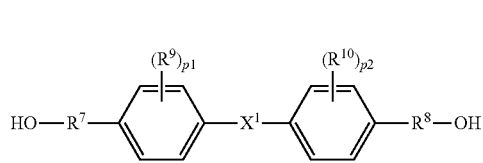

(ii-2)

wherein
$R^7$ and $R^8$ are independently —$(CR^{11}R^{12})_{q1}$— or —$(\text{—O—}(CR^{11}R^{12})_{q2}\text{—})_{q3}$— wherein $R^{11}$ and $R^{12}$ are independently H or a $C_{1-6}$ alkyl group, q1 is an integer of 0 or more and 10 or less, q2 is an integer of 1 or more and 10 or less, q3 is an integer of 1 or more and 10 or less, and when q1 or q2 is an integer of 2 or more, a plurality of $R^{11}$ or $R^{12}$ are the same as or different from each other,
$R^9$ and $R^{10}$ are independently a halogeno group, a $C_{1-20}$ aliphatic hydrocarbon group, a $C_{1-20}$ alkoxy group, a $C_{3-20}$ cycloalkyl group, a $C_{6-20}$ aromatic hydrocarbon group, a $C_{7-20}$ aralkyl group, a $C_{6-20}$ aromatic hydrocarbon oxy group or a $C_{3-20}$ cycloalkoxy group,
$X^1$ is a single bond or the following group:

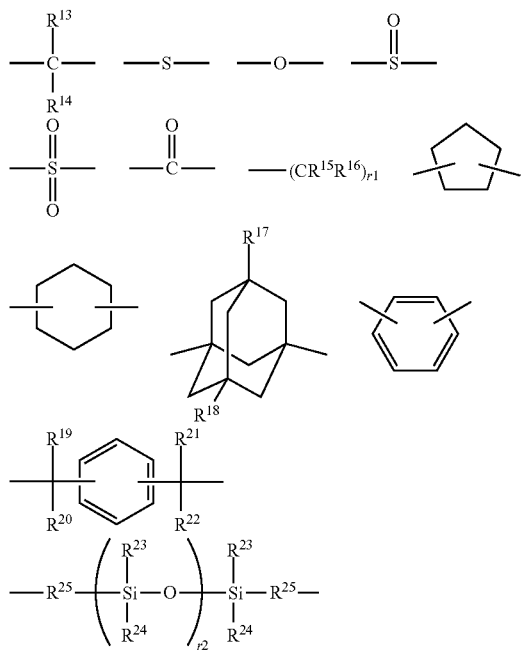

(wherein
$R^{13}$ and $R^{14}$ are independently H, a halogeno group, a $C_{1-20}$ aliphatic hydrocarbon group optionally having a substituent α, a $C_{1-20}$ alkoxy group optionally having a substituent α, a $C_{6-20}$ aromatic hydrocarbon group optionally having a substituent β, or $R^{13}$ and $R^{14}$ are connected to from a $C_{3-20}$ carbon ring or a 5-12 membered hetero ring,
$R^{15}$ and $R^{16}$ are independently H or a $C_{1-5}$ alkyl group, and when r1 is an integer of 2 or more, a plurality of $R^{15}$ or $R^{16}$ are the same as or different from each other,
$R^{17}$ to $R^{24}$ are independently a halogeno group, a $C_{1-20}$ aliphatic hydrocarbon group optionally having a substituent α, a $C_{1-20}$ alkoxy group optionally having a substituent α or a $C_{6-12}$ aromatic hydrocarbon group optionally having a substituent β,
$R^{25}$ is a $C_{1-9}$ alkylene group optionally having a substituent α,
r2 is an integer of 1 or more and 20 or less,
r2 is an integer of 1 or more and 500 or less.)
p1 and p2 are independently integers of 0 or more and 4 or less.

An example of the —$(CR^{11}R^{12})_{q1}$— includes an ethylene group, i.e. —$CH_2CH_2$—, and an example of the —O—$(CR^{11}R^{12})_{q2}$— includes —O—$CH_2CH_2$— and —O—CH($CH_3$)$CH_2$—. When $R^7$ is —$(\text{—O—}(CR^{11}R^{12})_{q1}\text{—})_{q3}$, HO—$R^7$-Ph is not HO—$\{\text{—O—}(CR^{11}R^{12})_{q1}\text{-}\}_{q3}$-Ph but is HO—$(\text{—}(CR^{11}R^{12})_{q2}\text{—O—})_{q3}$-Ph in terms of stability.

An example of the $C_{5-20}$ carbon ring formed by connecting $R^{13}$ and $R^{14}$ includes a $C_{3-20}$ cycloalkyl group optionally having substituent β and a condensed ring of a cycloalkyl group and an aromatic hydrocarbon group. An example of the condensed ring includes acenaphthenyl and fluorenyl.

An example of the 5-12 membered hetero ring formed by connecting $R^{13}$ and $R^{14}$ includes oxiranyl, aziridinyl, tetrahydrofuranyl, tetrahydrothiophenyl, pyrrolidinyl, oxathiolanyl, piperidinyl and 1(3h)-isobenzofuranyl.

An example of the hydroxy group-containing compound (ii-2) specifically includes 4,4'-biphenyldiol, bis(4-hydroxyphenyl)methane, bis(2-hydroxyphenyl)methane, 2,4'-dihydroxydiphenylmethane, bis(4-hydroxyphenyl)ether, bis(4-hydroxyphenyl)sulfone, 2,4'-dihydroxydiphenylsulfone, bis(2-hydroxyphenyl)sulfone, bis(4-hydroxy-3-methylphenyl)sulfone, bis(4-hydroxyphenyl)sulfoxide, bis(4-hydroxyphenyl)sulfide, bis(4-hydroxyphenyl)ketone, 1,1-bis(4-hydroxyphenyl)ethane, 1,1-bis(4-hydroxyphenyl)-1-phenylethane, bis(4-hydroxyphenyl)diphenylmethane, 2,2-bis(4-hydroxyphenyl)propane, 2,2-bis(4-hydroxy-3-methylphenyl)propane, 1,1-bis(4-hydroxy-3-methylphenyl)ethane, bis(4-hydroxy-3-methylphenyl)methane, 2,2-bis(4-hydroxy-3-t-butylphenyl)propane, 2,2-bis(4-hydroxyphenyl)butane, 1,1-bis(4-hydroxyphenyl)cyclohexane, 1,1-bis(4-hydroxy-3-methylphenyl)cyclohexane, 1,1-bis(4-hydroxyphenyl)cycloundecane, 1,1-bis(4-hydroxyphenyl)cyclododecane, 2,2-bis(4-hydroxy-3-allylphenyl)propane, 3,3,5-trimethyl-1,1-bis(4-hydroxyphenyl)cyclohexane, 9,9-bis(4-hydroxy-3-ethylphenyl)fluorene, 9,9-bis(4-hydroxy-3-methylphenyl)fluorene, 9,9-bis(4-hydroxyphenyl)fluorene, α,ω-bis[3-(o-hydroxyphenyl)propyl]polydimethyldiphenyl random copolymerized siloxane, α,ω-bis[3-(o-hydroxyphenyl)propyl]polydimethylsiloxane, 4,4'-[1,4-phenylenebis(1-methylethylidene)]bisphenol, 4,4'-[1,3-phenylenebis(1-methylethylidene)]bisphenol, 2,2-bis(4-hydroxyphenyl)butane, 1,1-bis(4-hydroxyphenyl)-2-ethylhexane, 1,1-bis(4-hydroxyphenyl)-2-methylpropane, 2,2-bis(4-hydroxyphenyl)-4-methylpentane, 1,1-bis(4-hydroxyphenyl)decane, 1,3-bis(4-hydroxyphenyl)-5,7-dimethyladamantane, 9,9-bis[4-(2-hydroxyethoxy)phenyl]fluorene, 9,9-bis[4-(2-hydroxyethoxy)-3-methylphenyl]

fluorene, 9,9-bis[4-(2-hydroxyethoxy)-3-t-butylphenyl] fluorene, 9,9-bis[4-(2-hydroxyethoxy)-3-isopropylphenyl] fluorene, 9,9-bis[4-(2-hydroxyethoxy)-3-cyclohexylphenyl] fluorene, 9,9-bis[4-(2-hydroxyethoxy)-3-phenylphenyl] fluorene, 4-(9-(4-hydroxyethoxyphenyl)-9H-fluorene-9-yl) phenol, 2,2-bis(4-(2-hydroxyethoxy)phenyl)propane, 4,4-bis(2-hydroxyethoxy)biphenyl, 2,2'(9H-fluorene-9,9'-diyl)bis(ethane-1-ol), 9H-fluorene-9,9-diylmethanol, 2,2'-(1,4-phenylene)bis(ethane-1-ol), 2,2'-(1,4-phenylene)bis(methane-1-ol), 2,2'-(1,4-phenylenebis(oxy))bis(ethane-1-ol), 1,1-bis(4-hydroxyphenyl)cyclododecane, 1,1-bis(4-hydroxy-3-methylphenyl)cyclododecane, 1,1-bis(4-hydroxy-3-phenylphenyl)cyclododecane, 1,1-bis(4-hydroxy-3-t-butylphenyl)cyclododecane, 1,1-bis(4-hydroxy-3-sec-butylphenyl)cyclododecane, 1,1-bis(4-hydroxy-3-allylphenyl)cyclododecane, 1,1-bis(4-hydroxy-3,5-dimethylphenyl)cyclododecane, 1,1-bis(4-hydroxy-3-fluorphenyl)cyclododecane, 1,1-bis(4-hydroxy-3-chlorophenyl)cyclododecane, 1,1-bis(4-hydroxy-3-bromophenyl)cyclododecane, 7-ethyl-1,1-bis(4-hydroxyphenyl)cyclododecane and 5,6-dimethyl-1,1-bis(4-hydroxyphenyl)cyclododecane.

Among the above examples, 4,4'-biphenyldiol, bis(4-hydroxyphenyl)methane, bis(2-hydroxyphenyl)methane, 2,4'-dihydroxydiphenylmethane, bis(4-hydroxyphenyl)ether, 2,2-bis(4-hydroxyphenyl)propane, 2,2-bis(4-hydroxy-3-methylphenyl)propane, 1,1-bis(4-hydroxyphenyl)cyclohexane, 9,9-bis[4-(2-hydroxyethoxy)phenyl]fluorene, 9,9-bis[4-(2-hydroxyethoxy)-3-phenylphenyl]fluorene, 1,1-bis(4-hydroxyphenyl)cyclododecane and 1,1-bis(4-hydroxy-3-methylphenyl)cyclododecane are particularly preferred. Further, the typical hydroxy group-containing compound (ii-2) is described as follows.

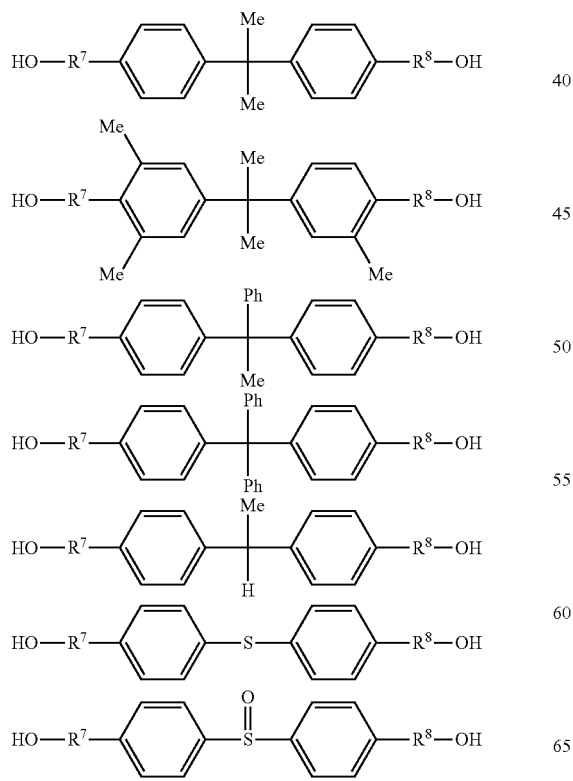

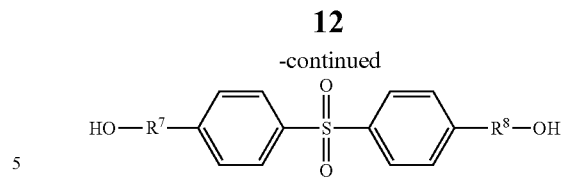

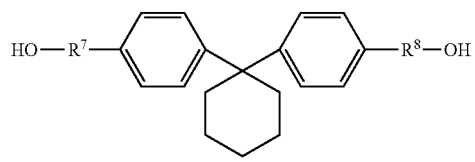

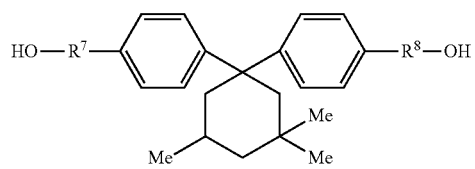

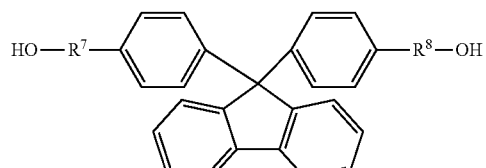

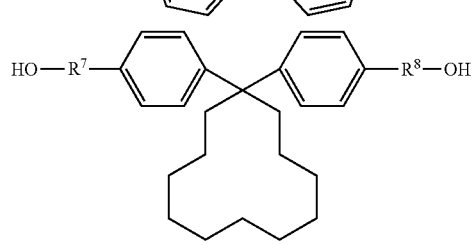

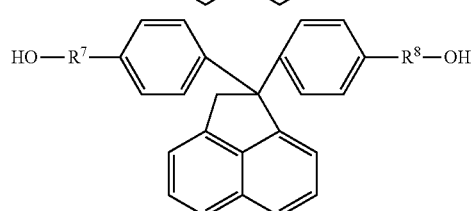

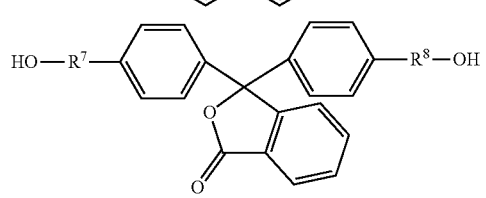

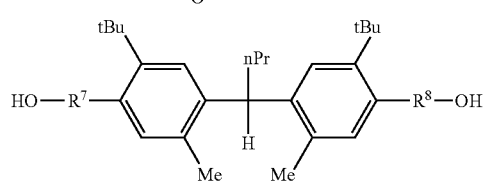

Bisphenol A, Bisphenol AP, Bisphenol B, Bisphenol BP, Bisphenol E, Bisphenol F, Bisphenol TMC and Bisphenol Z may be excluded from the diol compound ($I^1$) in some cases.

An example of the hydroxy group-containing compound (ii) includes the following hydroxy group-containing compound (ii-3):

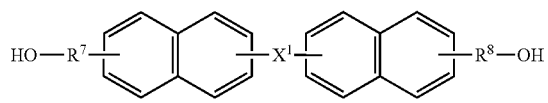

(ii-3)

wherein $R^7$, $R^8$ and $X^1$ have the same meanings as the above.

An example of the hydroxy group-containing compound (ii-3) specifically includes 9,9-bis[6-(1-hydroxymethoxy)naphthalene-2-yl]fluorene, 9,9-bis[6-(2-hydroxyethoxy)naphthalene-2-yl]fluorene, 9,9-bis[6-(3-hydroxypropoxy)naphthalene-2-yl]fluorene and 9,9-bis[6-(4-hydroxybutoxy)naphthalene-2-yl]fluorene. The hydroxy group-containing compound (ii-3) is particularly preferably 9,9-bis[6-(2-hydroxyethoxy)naphthalene-2-yl]fluorene.

An example of the hydroxy group-containing compound (ii-3) specifically includes the binaphthalene diol compound represented by the following formula:

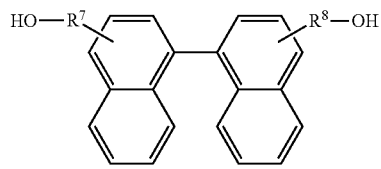

wherein $R^7$ and $R^8$ have the same meanings as the above.

An example of the binaphthalene diol compound includes 2,2'-bis(1-hydroxymethoxy)-1,1'-binaphthalene, 2,2'-bis(2-hydroxyethoxy)-1,1'-binaphthalene, 2,2'-bis(3-hydroxypropyloxy)-1,1'-binaphthalene and 2,2'-bis(4-hydroxybutoxy)-1,1'-binaphthalene. In particular, 2,2'-bis(2-hydroxyethoxy)-1,1'-binaphthalene is preferred.

An example of the hydroxy group-containing compound (ii) includes the following hydroxy group-containing compound (ii-4):

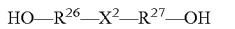

HO—$R^{26}$—$X^2$—$R^{27}$—OH    (ii-4)

wherein $R^{26}$ and $R^{27}$ are independently —$(CR^{11}R^{12})_{m1}$— or —$(-O-(CR^{11}R^{12})_{m2}-)_{m3}$— wherein $R^{11}$ and $R^{12}$ have the same meanings as the above, m1 is an integer of 1 or more and 10 or less, m2 is an integer of 1 or more and 10 or less, m3 is an integer of 1 or more and 10 or less, and when m1 or m2 is an integer of 2 or more, a plurality of $R^{11}$ or $R^{12}$ are the same as or different from each other, $X^2$ is a divalent group comprising 1 or more hydrocarbon rings or hetero rings.

An example of —$(CR^{11}R^{12})_{m1}$— includes ethylene group, i.e. —$CH_2CH_2$—, and an example of —O—$(CR^{11}R^{12})_{m2}$— includes —O—$CH_2CH_2$— and —O—$CH(CH_3)CH_2$—. When $R^{26}$ is —$(-O-(CR^{11}R^{12})_{m2}-)_{m3}$, HO—$R^{26}$—$X^3$— is not HO—$(-O-(CR^{11}R^{12})_{m2}-)_{m3}$—$X^2$— but is HO—$(-(CR^{11}R^{12})_{m2}-O-)_{m3}$—$X^2$— in terms of stability.

An example of the divalent group comprising 1 or more hydrocarbon rings or hetero rings includes a divalent $C_{6-32}$ aromatic hydrocarbon group optionally having substituent β, a $C_{3-20}$ cycloalkylene group optionally having substituent β, a 5-20 membered saturated heterocyclylene group optionally having substituent β, and a divalent group formed by connecting two or more groups selected from a $C_6$-32 aromatic hydrocarbon group optionally having substituent β, a $C_{3-20}$ cycloalkyl group optionally having substituent β and a 5-20 membered saturated heterocyclic group optionally having substituent β.

The divalent $C_{6-32}$ aromatic hydrocarbon group may contain a hetero atom selected from an oxygen atom, a sulfur atom and a nitrogen atom as long as the group totally exhibits aromaticity. An example of the divalent $C_{6-32}$ aromatic hydrocarbon group includes the following groups but is not particularly restricted thereto.

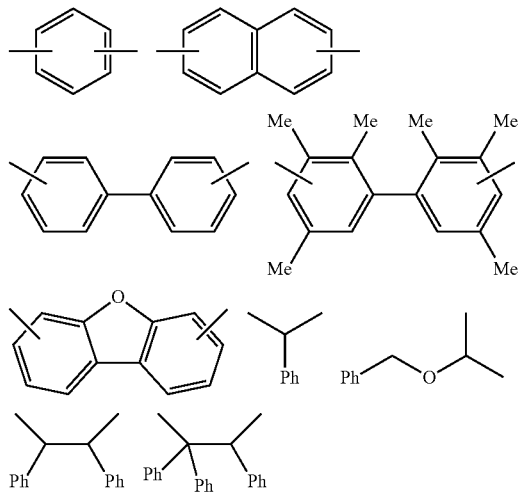

An example of the $C_{3-20}$ cycloalkylene group includes the following groups but is not particularly restricted thereto.

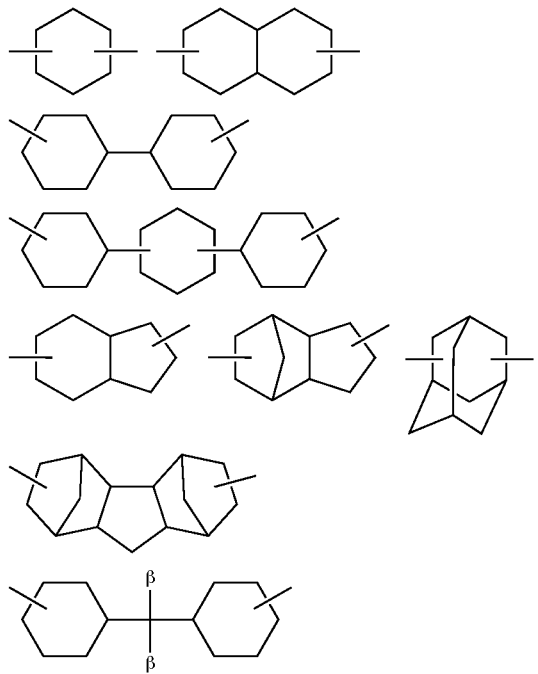

An example of the 5-20 membered saturated heterocyclylene group includes the following groups but is not particularly restricted thereto.

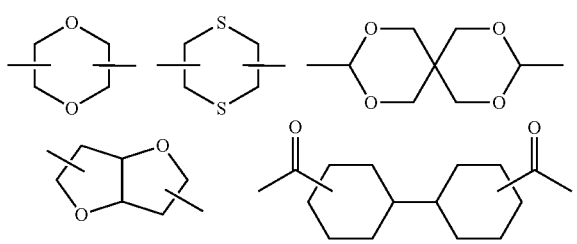

An example of the divalent group formed by connecting two or more groups selected from the $C_6$-32 aromatic hydrocarbon group, the $C_3$-20 cycloalkyl group and the 5-20 membered heterocyclic group includes the following groups but is not particularly restricted thereto.

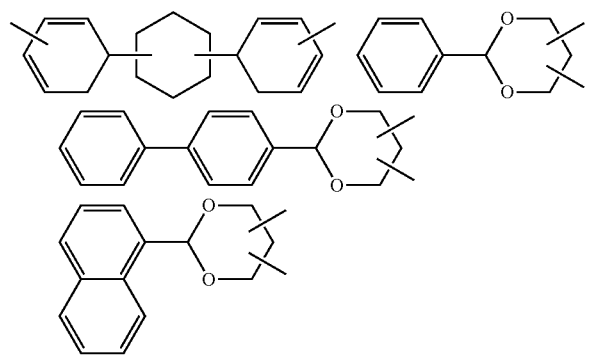

An example of the hydroxy group-containing compound (ii) includes the following hydroxy group-containing compound (ii-5):

(ii-5)

wherein $R^6$ and n have the same meanings as the above.

One kind of the hydroxy group-containing compound (ii) may be used by itself, or two or more kinds of the hydroxy group-containing compound (ii) may be used in combination. For example, when two kinds of the hydroxy group-containing compound (ii) are used in combination, a random polycarbonate can be synthesized. It is however preferred to use only one kind of the hydroxy group-containing compound (ii) by itself in terms of a production efficiency or the like. When two or more kinds of the diol compounds are used, the number of the diol compound is preferably 5 or less, more preferably 3 or less, and even more preferably 2. When two or more kinds of the diol compounds are used to be copolymerized by the present invention method, a range of a physical property of the obtained polycarbonate can be enlarged and the physical property can be easily adjusted.

A molar ratio of a total usage amount of the hydroxy group-containing compound to 1 mole of the halogenated methane in the reaction composition is adjusted to 0.05 or more. Even when a base is not used, the reaction successfully proceeds in the present invention by using a relatively large amount of the hydroxy group-containing compound. The hydroxy group-containing compound may be added without irradiating a light after irradiating a high energy light to the composition. The above-described molar ratio corresponds to a molar ratio of a total usage amount of the hydroxy group-containing compound added to the reaction mixture from the start to the completion of the reaction. In particular, when the hydroxy group-containing compound is a solid under an atmospheric temperature, it may be difficult in some cases to dissolve a relatively large amount of the hydroxy group-containing compound in the halogenated methane. In such a case, the hydroxy group-containing compound is preferably added without irradiating a light after irradiating a high energy light to the composition. The above-described molar ratio is preferably 0.1 or more, 0.2 or more, 0.4 or more or 0.5 or more, and more preferably 0.8 or more. The molar ratio may be 1.0 or more or 1.5 or more. When the above-described molar ratio is excessively large and the hydroxy group-containing compound is a solid, a problem of a solubility may arise; therefore, the molar ratio is preferably 20 or less, more preferably 10 or less, and even more preferably 5.0 or less.

When a halogenated carbonyl or a halogenated carbonyl-like compound is involved in the reaction, a nucleophilicity of the hydroxy group may be decreased in some cases due to an interaction between the hydroxy group of the hydroxy group-containing compound and the halogenated carbonyl compound. In general, a base is generally used in such a case. On the one hand, for example, when a base remains in a polycarbonate derivative, the remaining base may cause a coloration and a decomposition in some cases. The reaction proceeds in the present invention without using a base by using a relatively large amount of the hydroxy group-containing compound. In other words, the composition to be subjected to the photoreaction in the present invention contains the halogenated methane and the hydroxy group-containing compound but does not contain a base. The term "base" in this disclosure means a substance capable of neutralizing an acid generated by a decomposition of the halogenated methane, and has a function to interact with the hydroxy group of the hydroxy group-containing compound. As a result, a nucleophilicity of the hydroxy group is increased to accelerate the reaction.

3. Reaction Condition

The present invention method comprises a step of irradiating a high energy light to a composition comprising the halogenated methane and the hydroxy group-containing compound in the presence of oxygen.

A manner to mix the halogenated methane and the hydroxy group-containing compound is not particularly restricted. For example, total amount of each compound may be preliminarily mixed in a reaction vessel, or the compounds may be added in several portions or continuously added at any speed. When one or both of the halogenated methane and the hydroxy group-containing compound are not liquid in an atmospheric temperature and an atmospheric pressure, a solvent which can appropriately dissolve the raw material compounds and which does not inhibit the present invention reaction may be used. An example of such a solvent includes an aliphatic hydrocarbon solvent such as n-hexane; an aromatic hydrocarbon solvent such as benzene, toluene, xylene and chlorobenzene; an ether solvent such as diethyl ether, tetrahydrofuran and dioxane; and a nitrile solvent such as acetonitrile.

An oxygen source may be a gas containing oxygen, and for example, air or purified oxygen may be used. Purified oxygen may be mixed with an inert gas such as nitrogen and argon to be used. It is preferred to use air in terms of cost and easiness. An oxygen content in the gas used as an oxygen source is preferably about 15 vol % or more and about 100 vol % or less in terms of high decomposition efficiency of the halogenated methane by an irradiation of a high energy light. The oxygen content may be appropriately determined depending on the kind of the halogenated methane or the like. For example, when a halogenated methane such as dichloromethane and chloroform is used as the halogenated methane, the oxygen content is preferably 15 vol % or more and 100 vol % or less. When a halogenated methane such as dibromomethane and bromoform is used, the oxygen content is preferably 90 vol % or more and 100 vol % or less. Even when oxygen having an oxygen content of 100 vol % is used, the oxygen content can be controlled in the above-described range by adjusting a flow rate of oxygen into the reaction system. A manner to supply a gas containing oxygen is not particularly restricted, and the gas may be supplied into the reaction system from an oxygen tank equipped with a flow rate adjustor or from an oxygen generating device.

The phrase "in the presence of oxygen" means any one of the state that the above-described each compound is contacted with oxygen and the state that there is oxygen in the above-described composition. The reaction of the present invention may be carried out under a stream of a gas containing oxygen but it is preferred to supply a gas containing oxygen into the composition by bubbling in terms of a high yield of the product.

An amount of an oxygen-containing gas may be appropriately determined depending on the amount of the halogenated methane or a shape of a reaction vessel. For example, an amount of the gas supplied to a reaction vessel per 1 minute to the halogenated methane in the reaction vessel is preferably 5 times or more by volume. The ratio is more preferably 25 times or more by volume, and even more preferably 50 times or more by volume. The upper limit of the ratio is not particularly restricted, and the ratio is preferably 500 times or less by volume, more preferably 250 times or less by volume, and even more preferably 150 times or less by volume. The amount of oxygen supplied to a reaction vessel per 1 minute to the $C_{1-4}$ hydrocarbon compound in the reaction vessel may be 5 times or more by volume and 25 times or less by volume. When an amount of the gas is excessively large, the $C_{1-4}$ hydrocarbon compound may be possibly volatilized, but when the amount is excessively small, it may possibly become difficult to develop the reaction. For example, a supply rate of oxygen may be 0.01 L/min or more and 10 L/min or less per 4 mL of the halogenated methane compound.

The high energy light irradiated on the composition is preferably a light containing a short wavelength light, more preferably a light containing ultraviolet light, and more specifically, preferably a light containing a light having a wavelength of 180 nm or more and 500 nm or less, more specifically a light having a peak wavelength of 180 nm or more and 500 nm or less. A wavelength or a peak wavelength of the high energy light may be appropriately determined depending on the kind of the halogenated methane, and is more preferably 400 nm or less and even more preferably 300 nm or less. When the irradiated light contains a light of the above-described wavelength range, the halogenated methane undergoes oxidative photodecomposition in an efficient fashion. For example, the light containing UV-B having a wavelength of 280 nm or more and 315 nm or less and/or UV-C having a wavelength of 180 nm or more and 280 nm or less or the light having a peak wavelength included in the ranges can be used, and the light containing UV-C having a wavelength of 180 nm or more and 280 nm or less or the light having a peak wavelength included in the range is preferably used.

A means for the light irradiation is not particularly restricted as long as the light having the above-described wavelength can be irradiated by the means. An example of a light source of the light having such a wavelength range includes sunlight, low pressure mercury lamp, medium pressure mercury lamp, high pressure mercury lamp, ultra-high pressure mercury lamp, chemical lamp, black light lamp, metal halide lamp and LED lamp. A low pressure mercury lamp is preferably used in terms of a reaction efficiency and a cost.

The condition such as a strength of the light to be irradiated, an irradiation time or the like may be appropriately determined depending on the kind and usage amount of the raw material compounds. For example, a light strength at a shortest distance position of the composition from the light source is preferably 1 mW/cm$^2$ or more and 50 mW/cm$^2$ or less. An irradiation time is preferably 0.5 hours or more and 10 hours or less, more preferably 1 hour or more and 6 hours or less, and even more preferably 2 hours or more and 4 hours or less. A manner to irradiate the light is not also particularly restricted, and any manners can be selected. For example, the light may be continuously irradiated from the reaction initiation to the reaction completion, irradiation and un-irradiation of the light may be alternately repeated, and the light may be irradiated from the reaction initiation for a predetermined time only. When irradiation and un-irradiation of the light may be alternately repeated, the reaction can be successfully accelerated by alternately repeating a halogeno-carbonylation of the hydroxy group-containing compound and a further reaction with the hydroxy group-containing compound due to an appropriate stoicheiometric ratio of the hydroxy group-containing compound and the halogenated carbonyl compound thereof. A shortest distance between the light source and the halogenated methane is preferably 1 m or less, more preferably 50 cm or less, and even more preferably 10 cm or less or 5 cm or less. The lower limit of the shortest distance is not particularly restricted and may be 0 cm, in other words, the light source may be immersed into the halogenated methane.

A temperature during the reaction is not particularly restricted and may be appropriately adjusted, and for example, may be adjusted to 0° C. or higher and 50° C. or lower. The temperature is more preferably 10° C. or higher, even more preferably 20° C. or higher, and more preferably 40° C. or lower, even more preferably 30° C. or lower.

A part of an amount of the hydroxy group-containing compound may be added to the reaction mixture after the irradiation of the high energy light is stopped. The decomposition of the hydroxy group-containing compound, the product of the degradant of the halogeneted methane and the hydroxy group-containing compound, and/or the carbonate derivative as the target compound due to the high energy light can be suppressed by this embodiment.

In addition, the irradiation of the high energy light and the supply of oxygen may be stopped and the temperature may be increased after the reaction between the halogenated methane and the hydroxy group-containing compound. The halogenated carbonyl generated by photooxidative degradation of the halogenated methane can be discharged from the reaction mixture by this step. The temperature of this step is not particularly restricted as long as an excessive amount of the halogenated carbonyl can be reduced, and for example, can be adjusted to 40° C. or higher and 80° C. or lower.

A reaction apparatus usable in the production method of the present invention is exemplified by a reaction vessel equipped with a light irradiation means. A reaction apparatus may be equipped with a stirring device and a temperature control means. One embodiment of a reaction apparatus usable in the production method of the present invention is shown in FIG. 1. The reaction apparatus shown in FIG. 1 has a light irradiation means 1 in a cylindrical reaction vessel 6. The above-described raw material compounds are added into a cylindrical reaction vessel 6, and a light is irradiated by using a light irradiation means 1 while a gas containing oxygen is supplied into the cylindrical reaction vessel 6 or a gas containing oxygen is blown into the composition to cause bubbling (not shown in the figure) for the reaction. When a light irradiation means 1 is covered with a jacket 2 or the like, it is preferred that the jacket is composed of a material that allows passing the short wavelength light. A light may be irradiated from outside a reaction vessel. In such a case, the reaction vessel is composed of a material that allows passing the short wavelength light. A material that allows passing the short wavelength light is not particularly restricted as long as the effect of the present invention is not inhibited, and is preferably exemplified by quartz glass.

The product obtained by the reaction may be purified by a conventionally known method. An example of such a purification method includes distillation, removal of a raw material compound under reduced pressure, column chromatography, liquid separation, extraction, washing and recrystallization.

4. Produced Compound

In the present invention, when the hydroxy group-containing compound (ii) is used, the polycarbonate derivative (II-1) is produced or the cyclic carbonate derivative (II-2) is produced. The production ratio thereof is mainly dependent on a distance between the two hydroxy groups of the hydroxy group-containing compound (ii) and a flexibility of the chemical structure thereof. The ratio may be confirmed by a preliminary experiment or the like.

The linear carbonate derivative produced by the present invention method is useful as a non-aqueous solvent or the like. For example, the linear carbonate can be used as a solvent of an electrolyte for a lithium ion secondary battery. In addition, the polycarbonate is useful as an excellent engineering plastic.

The present application claims the benefit of the priority date of Japanese patent application No. 2018-215003 filed on Nov. 15, 2018. All of the contents of the Japanese patent application No. 2018-215003 filed on Nov. 15, 2018, are incorporated by reference herein.

EXAMPLES

Hereinafter, the examples are described to demonstrate the present invention more specifically, but the present invention is in no way restricted by the examples, and the examples can be appropriately modified to be carried out within a range which adapts to the contents of this specification. Such a modified example is also included in the range of the present invention.

Examples 1 to 4: Reaction of Aliphatic Alcohol

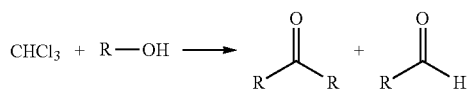

A quartz glass jacket having a diameter of 30 mm was inserted into a cylindrical reaction vessel having a diameter of 42 mm and a volume of 100 mL, and a low pressure mercury lamp ("UVL20PH-6" manufactured by SEN Light, 20 W, φ24x120 mm) was further inserted into the quartz glass jacket to construct a reaction system. A schematic picture of the reaction system is shown as FIG. 1. The light irradiated from the low pressure mercury lamp contained UV-C having a wavelength of 254 nm, and the illumination intensity of the light having a wavelength of 254 nm at the position 5 mm from the tube wall was 6.23 to 9.07 mW/cm$^2$. In the reaction vessel, purified chloroform (20 mL, 250 mmol) and an aliphatic alcohol described in Table 1 (250 mmol) were added and mixed under stirring. Oxygen gas was blown into the stirred reaction mixture at a flow rate of 0.5 L/min at 50° C. to cause bubbling, and a high energy light containing UV-C was irradiated. Then, the reaction mixture was analyzed by $^1$H NMR and the yield was calculated. The result is shown in Table 1.

TABLE 1

| Example | Alcohol (R—OH) R | Reaction time | Yield Carbonate | Aldehyde |
|---|---|---|---|---|
| 1 | Ethyl | 61 h | 39% | 19% |
| 2 | n-Propyl | 82 h | 29% | 18% |
| 3 | Isopropyl | 94 h | 12% | 9% |
| 4 | n-Butyl | 82 h | 16% | 18% |

It was experimentally demonstrated by the result shown in Table 1 that even when a base is not used, a carbonate can be easily synthesized from chloroform and an alcohol. The aldehyde may be generated by the photolysis of a chloroformate ester.

Examples 5 to 7: Synthesis of Ethylene Carbonate

In the reaction vessel of the reaction system used in Example 1, purified chloroform (16 mL, 200 mmol) and ethylene glycol (5.6 mL, 100 mmol) were added. Oxygen gas was blown into the stirred mixture at a flow rate of 0.5 L/min at the temperature described in Table 2 to cause bubbling, and a high energy light containing UV-C was irradiated.

Water and dichloromethane were added to the reaction mixture after 8 hours, and the aqueous phase and the organic phase were separated. The organic phase was concentrated at 80° C. under reduced pressure to obtain ethylene carbonate as white powder. The yield is shown in Table 2.

TABLE 2

| Example | Reaction Temperature | Yield |
|---|---|---|
| 5 | 0° C. | 40% |
| 6 | 20° C. | 87% |
| 7 | 25° C. | 70% |

In addition, the reaction temperature was changed to 50° C., samples were collected from the reaction mixture every 30 minutes up to 6 hours and analyzed by $^1$H NMR to obtain an integral ratio of a peak area of the methylene group proton in the ethylene carbonate to the methylene group proton in the ethylene glycol. The result is shown in FIG. 2.

It was confirmed as the result shown in FIG. 2 that ethylene carbonate is produced with the development of the reaction but an amount of ethylene carbonate tends to be decreased in the case of a long reaction time. The reason may be that when an amount of ethylene glycol is large, a ring-opening polymerization reaction as the following formula proceeds to generate polycarbonate diol in the case of a long reaction time from the time-course changes of the $^1$H NMR spectra.

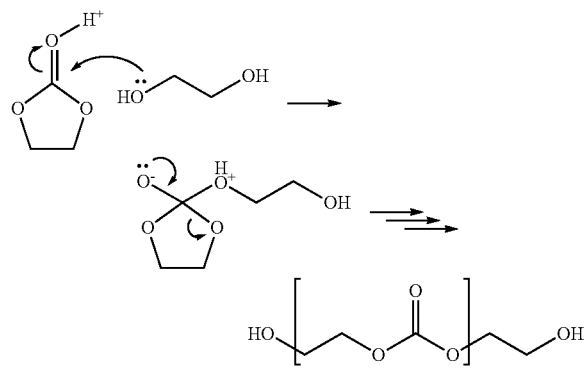

Separately, the reaction time was changed to 3.5 hours and ethylene carbonate was isolated in the above-described conditions; as a result, the yield was 23%. In addition, the polymer yield obtained from the analysis result by $^1$H NMR was 14%, and 40% of ethylene glycol could be recovered.

Examples 8 to 10: Synthesis of Ethylene Carbonate

Ethylene carbonate was synthesized similarly to the above-described Examples 5 to 7 except that a usage amount of chloroform was changed to 8 mL (100 mmol) and the molar ratio of chloroform and ethylene glycol was adjusted to 1:1. The result is shown in Table 3.

TABLE 3

| Example | Reaction temperature | Yield |
|---------|---------------------|-------|
| 8       | 0° C.               | 62%   |
| 9       | 20° C.              | 50%   |
| 10      | 25° C.              | 32%   |

Example 11: Synthesis of PTMG polycarbonate

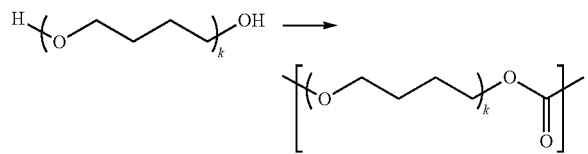

Purified chloroform (4 mL, 50 mmol) and poly(tetramethylene ether)glycol ("PolyTHF2000S" manufactured by BASF, molecular weight: 2000 g/mol, the "k" in the above formula represents repetition.) (10.3 g, 5 mmol) were added in the reaction vessel of the reaction system used in Example 1, and the mixture was mixed under stirring. Oxygen gas was blown into the stirred reaction mixture at a flow rate of 1 L/min at 20° C. to cause bubbling, and a high energy light containing UV-C was irradiated for 6 hours.

Then, the power of the low pressure mercury lamp was turned off, PTMG2000 (10.3 g, 5 mmol) was further added, and the mixture was stirred at 120° C. for 3 hours.

Water and chloroform were added to the reaction mixture, and then the organic phase and the aqueous phase were separated. The organic phase was dried using anhydrous sodium sulfate and concentrated under reduced pressure at 50° C. for 2 hours to obtain yellow liquid (yield amount: 15.1 g, yield: 72%). The obtained liquid was analyzed by $^1$H NMR; as a result, it was confirmed that the target compound was produced.

The obtained liquid was analyzed by gel permeation chromatography (GPC) in the following conditions to measure the molecular weight. The result is shown in Table 4.

Apparatus: High speed GPC system ("HLC-8320GPC" manufactured by Tosoh)
Column: "SuperMultipoer HZ-M" (4.6 mm×150 mm, 3 columns in series, manufactured by Tosoh)
Moving phase: chloroform Flow rate: 0.35 mL/min
Oven temperature: 40° C. Concentration: 0.2 w/v %
Injection amount: 10 μL Standard of molecular weight: polystyrene
Detector: RI

TABLE 4

| Mw     | Mn    | Mw/Mn |
|--------|-------|-------|
| 13,300 | 6,600 | 2.03  |

Example 12: Synthesis of 1,3-Propane Diol Polycarbonate

HO~~~OH →

Purified chloroform (8 mL, 100 mmol) and 1,3-propanediol (100 mmol) were added in the reaction vessel of the reaction system used in Example 1, and the mixture was mixed under stirring. Oxygen gas was blown into the stirred reaction mixture at a flow rate of 0.5 L/min at 50° C. to cause bubbling, and a high energy light containing UV-C was irradiated for 10 minutes. Then, the power of the low pressure mercury lamp was turned off, and the mixture was stirred without irradiating a high energy light for 10 minutes. The cycle was repeated 24 times. Purified chloroform (8 mL, 100 mmol) was further respectively added 2 hours, 4 hours and 6 hours after the start of the reaction to compensate evaporated or decomposed chloroform. After the reaction, the reaction mixture was dried at 50° C. under reduced pressure for 2 hours to obtain colorless liquid. The molecular weight was determined in the same conditions as Example 11. The result is shown in Table 5.

TABLE 5

| Mw  | Mn  | Mw/Mn |
|-----|-----|-------|
| 140 | 120 | 1.13  |

Example 13: Synthesis of 1,4-Butanediol Polycarbonate

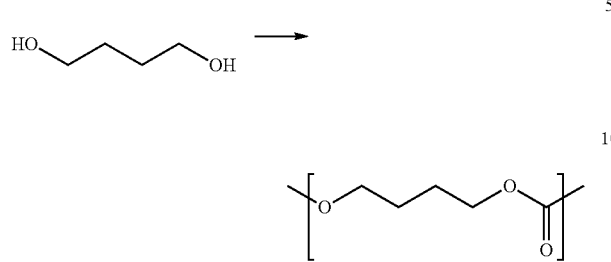

Purified chloroform (8 mL, 100 mmol) and 1,4-butanediol (100 mmol) were added in the reaction vessel of the reaction system used in Example 1, and the mixture was mixed under stirring. Oxygen gas was blown into the stirred reaction mixture at a flow rate of 0.5 L/min at 20° C. to cause bubbling, and a high energy light containing UV-C was irradiated for 10 hours. Then, the power of the low pressure mercury lamp was turned off, and the mixture was stirred without irradiating a high energy light at room temperature for 12 hours.

After the reaction, the reaction mixture was dried at 50° C. under reduced pressure for 2 hours to obtain yellow liquid. The molecular weight was determined in the same conditions as Example 11. The result is shown in Table 6.

TABLE 6

| Mw | Mn | Mw/Mn |
|---|---|---|
| 330 | 140 | 2.41 |

Example 14: Synthesis of 4-hydroxymethylethylene Carbonate

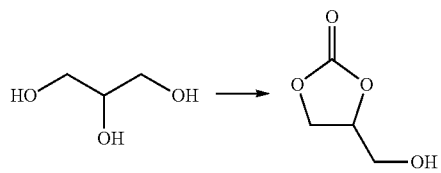 [SMILES: OCC(O)CO ; O=C1OCC(CO)O1]

Purified chloroform (24 mL, 300 mmol) and glycerin (100 mmol) were added in the reaction vessel of the reaction system used in Example 1, and the mixture was mixed under stirring. Oxygen gas was blown into the stirred reaction mixture at a flow rate of 0.5 L/min at 50° C. to cause bubbling, and a high energy light containing UV-C was irradiated for 3 hours.

After the reaction, acetone was added to the reaction mixture as an internal standard, and the mixture was analyzed by $^1$H NMR; as a result, it was confirmed that 4-hydroxymethylethylene carbonate as the target compound was produced (yield: 65%).

Example 15: Synthesis of PTMG Polycarbonate

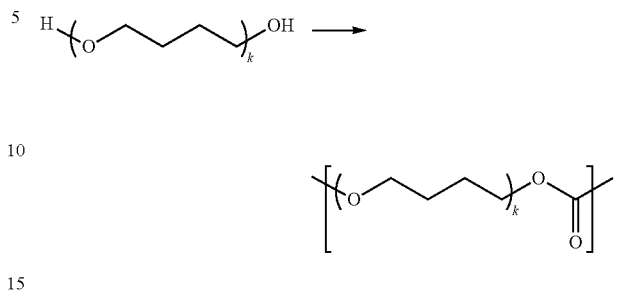

Purified chloroform (1 mL, 12.5 mmol) and PGP-4C$_3$ poly(tetramethylene ether)glycol ("PolyTHF2000S" manufactured by BASF, molecular weight: 2000 g/mol, the "k" in the above formula represents repetition.) (10.3 g, 5 mmol) were added in the reaction vessel of the reaction system used in Example 1, and the mixture was mixed under stirring. Oxygen gas was blown into the stirred reaction mixture at a flow rate of 1 L/min at 20° C. to cause bubbling, and a high energy light containing UV-C was irradiated for 2 hours.

Then, the power of the low pressure mercury lamp was turned off, PTMG2000 (10.3 g, 5 mmol) was further added, and the mixture was stirred under argon atmosphere at 80° C. for 17 hours. The mixture was analyzed by $^1$H NMR; as a result, it was confirmed that the target compound was generated (yield amount: 16.1 g, yield: 77%). The reaction liquid became a solid at room temperature. The obtained solid was analyzed by gel permeation chromatography (GPC) in the same conditions as Example 11 to determine the molecular weight. The result is shown in Table 7.

TABLE 7

| Mw | Mn | Mw/Mn |
|---|---|---|
| 17,700 | 6,400 | 2.76 |

Example 16: Synthesis of Ethylene Carbonate

The amounts described in Table 8 of purified chloroform and ethylene glycol (EG) were added in the reaction vessel of the reaction system used in Example 1, oxygen gas was blown into the stirred mixture at a flow rate of 0.5 L/min at 20° C. to cause bubbling, and a high energy light containing UV-C was irradiated for 3 hours.

The light irradiation was stopped after 1 hour, and the mixture was further stirred at 50° C. for 1 hour. Then, the reaction mixture was analyzed by $^1$H NMR to determine ratios of ethylene carbonate, carbonate diol, chloroformate ester and unreacted ethylene glycol to the used ethylene glycol. The yields were calculated on the basis of a relatively smaller amount of the compound, i.e. chloroform in Experimental numbers 1 and 2 and ethylene glycol in Experimental numbers 3 and 4, since the phosgene generated from chloroform and ethylene glycol must be reacted in a ratio of 1:1 in the reaction of this experiment. The result is shown in Table 8.

TABLE 8

| Experimental number | Raw material compound | | | Yield | | | |
| --- | --- | --- | --- | --- | --- | --- | --- |
| | CHCl₃ [mmol] | EG [mmol] | EG/CHCl₃ | Ethylene carbonate | Carbonate diol | Choroformate ester | Remaining EG |
| 1 | 1 | 100 | 100 | 2% | 2.4% | — | 99% |
| 2 | 10 | 100 | 10 | 48% | 12% | — | 94% |
| 3 | 100 | 10 | 0.1 | 80% | — | 6.7% | 6.4% |
| 4 | 100 | 1 | 0.01 | 31% | — | 12% | 29% |

As the results of Experimental numbers 1 and 2 shown in Table 8, even when an amount of ethylene glycol was substantially excess to chloroform, the reaction proceeded. It was surprising that even when an amount of ethylene glycol was excessively large, the reaction proceeded, since an alcohol compound is used as a stabilizer of chloroform and a small amount of an alcohol compound is added in a chloroform product.

In addition, when a molar ratio of ethylene glycol as the hydroxy group-containing compound to 1 mole of chloroform as the halogenated methane was 0.1, the reaction successfully proceeded and ethylene carbonate as the target compound could be obtained with high yield as 80%.

On the one hand, when a molar ratio of ethylene glycol as the hydroxy group-containing compound to 1 mole of chloroform as the halogenated methane was 0.01, the reaction did not sufficiently proceed and the yield of ethylene carbonate as the target compound was low but the yield of chloroformate ester was relatively high. The reason for the result is not clear.

A carbonate derivative therefore may be successfully obtained by using the hydroxy group-containing compound of which molar ratio to 1 mole of the halogenated methane is 0.05 or more.

Example 17: Synthesis of BPEF Polycarbonate

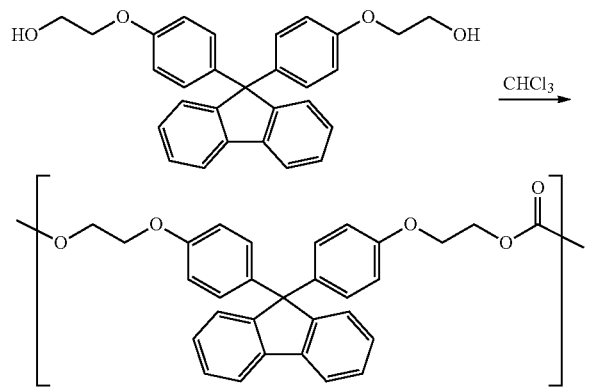

Purified chloroform (8 mL, 100 mmol) and 9,9-bis [4-(2-hydroxyethoxy)phenyl]fluorene (BPEF, manufactured by Taoka Chemical, 2.19 g, 5 mmol) were added in the reaction vessel of the reaction system used in Example 1, and the mixture was mixed under stirring. Oxygen gas was blown into the stirred reaction mixture at a flow rate of 1.0 L/min at 20° C. to cause bubbling, and a high energy light containing UV-C was irradiated for 3.5 hours.

Then, the power of the low pressure mercury lamp was turned off, and the reaction mixture was stirred at 50° C. for 1 hour. Then, BPEF (2.19 g, 5 mmol) was additionally added, and the mixture was stirred at 180° C. for 1 hour. Dichloromethane and methanol were added to the reaction mixture, and the generated precipitate was obtained by suction filtration and dried in vacuo to obtain polycarbonate as brown solid with yield of 63%. The product was identified by ¹H NMR and FT-IR. The obtained polycarbonate was analyzed by gel permeation chromatography (GPC) in the following conditions to measure the molecular weight. The result is shown in Table 9.

Apparatus: High speed chromatograph system ("MD-2060", "PU-2089", "LC-NetII/ADC", "CO-2060" manufactured by JASCO Corporation)

Column: "TSKgel G3000HR" (7.8 mm×300 mm), "TSKgel G4000HR" (7.8 mm×300 mm, 2 columns in series) manufactured by Tosoh Moving phase: THF Flow rate: 0.5 mL/min Oven temperature: 20° C. Concentration: 0.2 w/v %

Injection amount: 10 μL Standard of molecular weight: polystyrene

Detector: PDA

TABLE 9

| Mw | Mn | Mw/Mn |
| --- | --- | --- |
| 6,355 | 2,815 | 2.26 |

Example 18: Synthesis of PCPDM Polycarbonate

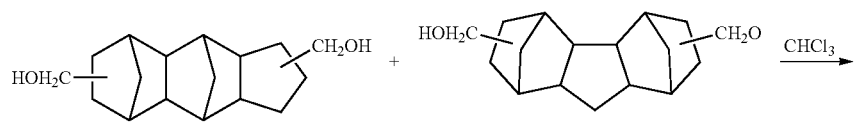

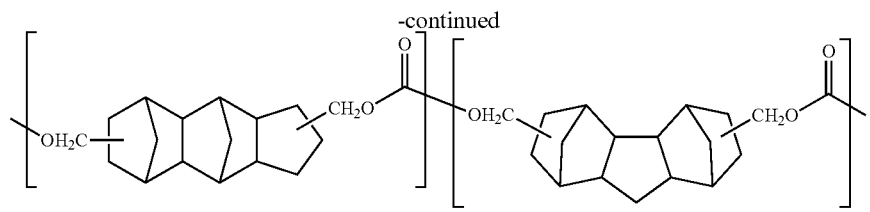

Purified chloroform (40 mL, 50 mmol) and pentacyclopentadecane dimethanol (PCPDM, manufactured by MITSUBISHI GAS CHEMICAL, 1.31 g, 5 mmol) were added in the reaction vessel of the reaction system used in Example 1, and the mixture was mixed under stirring. Oxygen gas was blown into the stirred reaction mixture at a flow rate of 1.0 L/min at 0° C. to cause bubbling, and a high energy light containing UV-C was irradiated for 2 hours. The temperature was increased to 20° C. to further conduct the reaction for 1 hour.

Then, the power of the low pressure mercury lamp was turned off, and the reaction mixture was stirred at 50° C. for 1 hour. Then, the reaction mixture was stirred at 120° C. for 1 hour and further at 160° C. for 1 hour. Chroloform and methanol were added to the reaction mixture, and the generated precipitate was obtained by suction filtration and dried in vacuo at 50° C. to obtain polycarbonate as light brown solid with yield of 51%. The product was identified by $^1$H NMR and FT-IR. The molecular weight was determined in the same conditions as Example 11. The result is shown in Table 10.

TABLE 10

| Mw | Mn | Mw/Mn |
|---|---|---|
| 3,050 | 1,560 | 1.954 |

Example 19: Synthesis of TCDDM Polycarbonate

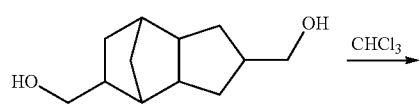

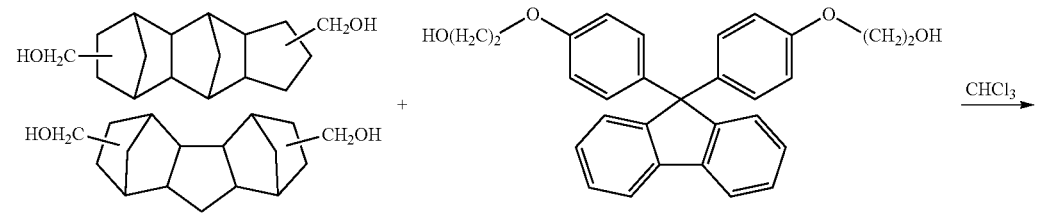

Purified chloroform (4 mL, 50 mmol) and tricyclo[5.2.1.0 (2,6)]decanedimethanol (TCDDM, manufactured by Oxea, 0.98 g, 5 mmol) were added in the reaction vessel of the reaction system used in Example 1, and the mixture was mixed under stirring. Oxygen gas was blown into the stirred reaction mixture at a flow rate of 1.0 L/min at 0° C. to cause bubbling, and a high energy light containing UV-C was irradiated for 3 hours.

Then, the power of the low pressure mercury lamp was turned off, and the reaction mixture was stirred at 50° C. for 1 hour. Then, TCDDM (0.82 g, 4.18 mmol) was additionally added, and the mixture was stirred at 120° C. for 1 hour and at 160° C. for 1 hour. Chloroform and methanol were added to the reaction mixture, and the generated precipitate was collected by suction filtration and dried in vacuo at 80° C. to obtain polycarbonate as brown solid with yield of 87%. The product was identified by $^1$H NMR and FT-IR. The molecular weight was determined in the same conditions as Example 11. The result is shown in Table 11.

TABLE 11

| Mw | Mn | Mw/Mn |
|---|---|---|
| 6,000 | 2,660 | 2.256 |

Example 20: Synthesis of Polycarbonate Copolymer

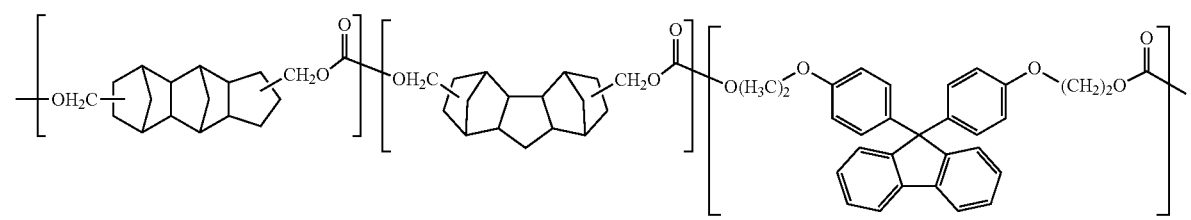

Purified chloroform (4 mL, 50 mmol), 9,9-bis[4-(2-hydroxyethoxy)phenyl]fluorene (BPEF, manufactured by Taoka Chemical, 2.19 g, 5 mmol) and pentacyclopentadecane dimethanol (PCPDM, manufactured by MITSUBISHI GAS CHEMICAL, 1.31 g, 5 mmol) were added in the reaction vessel of the reaction system used in Example 1, and the mixture was mixed under stirring. Oxygen gas was blown into the stirred reaction mixture at a flow rate of 1.0 L/min at 0° C. to cause bubbling, and a high energy light containing UV-C was irradiated for 3 hours.

Then, the power of the low pressure mercury lamp was turned off, and the reaction mixture was stirred at 50° C. for 1 hour. The reaction mixture was stirred under argon atmosphere at 120° C. for 1 hour. The temperature was increased to 200° C., and the reaction mixture was stirred for 1 hour. Dichloromethane and methanol were added to the reaction mixture, and the generated precipitate was collected by suction filtration and dried in vacuo to obtain polycarbonate as light brown solid with yield of 40%. It was confirmed that BPEF-PCPDM polycarbonate copolymer as the target compound was generated by analyzing the product by $^1$H NMR and FT-IR. The molecular weight was determined in the same conditions as Example 17. The result is shown in Table 12.

TABLE 12

| Mw | Mn | Mw/Mn |
|---|---|---|
| 3,360 | 1,488 | 2.26 |

Example 21: Synthesis of Polycarbonate Copolymer

C., and the reaction mixture was further stirred for 1 hour. The reaction mixture was left to stand still until the temperature was returned to room temperature; as a result, polycarbonate was obtained as brown solid with a yield of 95%. The product was identified by 1H-NMR. The molecular weight was determined in the same conditions as Example 17. The result is shown in Table 13.

TABLE 13

| Mw | Mn | Mw/Mn |
|---|---|---|
| 3,954 | 2,157 | 1.833 |

EXPLANATION OF REFERENCES

1: Light-irradiating means, 2: Jacket, 3: Water bath, 4: Stirring bar, 5: Heating medium or Cooling medium, 6: Cylindrical reaction vessel

The invention claimed is:
1. A method for producing a carbonate derivative,
the method consisting of an optional step of stirring a liquid composition comprising a halogenated methane and a hydroxy group-containing compound without irradiating a high energy light, and a step of irradiating the high energy light to the liquid composition in the presence of oxygen to produce the carbonate derivative, and optionally repeating the optional step of stirring and the step of irradiating,
wherein the liquid composition does not comprise a base,
wherein a molar ratio of a total usage amount of the hydroxy group-containing compound to 1 mole of the halogenated methane is 0.1 or more,

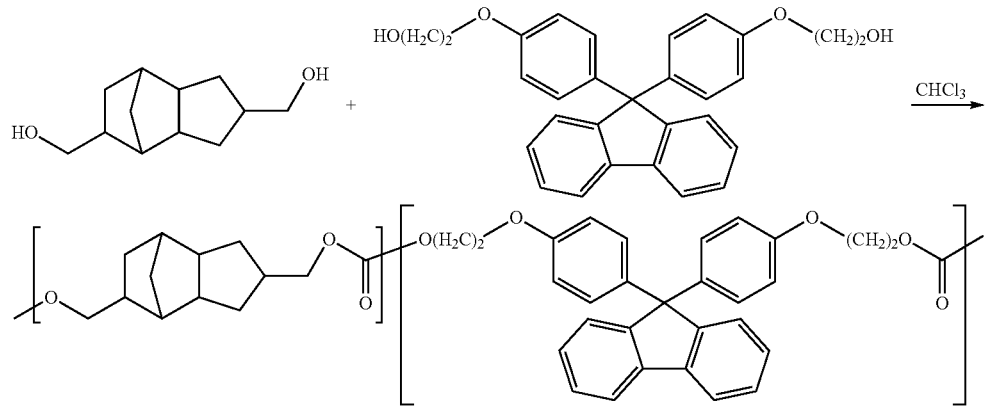

Purified chloroform (8 mL, 50 mmol), 9,9-bis[4-(2-hydroxyethoxy)phenyl]fluorene (BPEF, 2.19 g, 5 mmol) and tricyclo[5.2.1.0(2,6)]decanedimethanol (TCDDM, 0.98 g, 5 mmol) were added in the reaction vessel of the reaction system used in Example 1, and the mixture was mixed under stirring. Oxygen gas was blown into the stirred reaction mixture at a flow rate of 1.0 L/min at 0° C. to cause bubbling, and a high energy light containing UV-C was irradiated for 3 hours. The power of the lamp was turned off, and the reaction mixture was stirred at 50° C. for 1 hour.

TCDDM (0.98 g, 5 mmol) was additionally added to the mixture, and the mixture was stirred under argon atmosphere at 120° C. for 1 hour. The temperature was increased to 200° wherein the hydroxy group-containing compound is represented by the following formula (i) and the carbonate derivative is a linear carbonate derivative represented by the following formula (I), or
the hydroxy group-containing compound is represented by the following formula (ii) and the carbonate derivative is a carbonate derivative comprising a unit represented by the following formula (II-1) or a cyclic carbonate derivative represented by the following formula (II-2):

$$R^1\text{—OH} \qquad (i)$$

$$\text{HO—}R^2\text{—OH} \qquad (ii)$$

$$R^1-O-C(=O)-O-R^1 \quad (I)$$

$$[-O-R^2-O-C(=O)-] \quad (II\text{-}1)$$

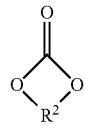

(II-2)

wherein
- $R^1$ is a monovalent $C_{1\text{-}200}$ organic group optionally comprising a hetero atom,
- $R^2$ is a divalent $C_{1\text{-}200}$ organic group optionally comprising a hetero atom.

2. The method according to claim 1, wherein the halogenated methane is chloroform.

3. The method according to claim 1, consisting of the step of stirring the composition without irradiating the high energy light.

4. The method according to claim 1, wherein the high energy light comprises a light having a wavelength of 180 nm or more and 280 nm or less.

5. The method according to claim 1, wherein two or more kinds of the hydroxy group-containing compound are used.

* * * * *